(12) United States Patent
Banchieri

(10) Patent No.: US 7,275,875 B1
(45) Date of Patent: Oct. 2, 2007

(54) UNIVERSAL INTERFACE FOR SINGLE-HANDED INSERTION OF CABLES

(75) Inventor: Michael J. Banchieri, Santa Clara, CA (US)

(73) Assignee: Stryker Corporation, Kalamazoo, MI (US)

( * ) Notice: Subject to any disclaimer, the term of this patent is extended or adjusted under 35 U.S.C. 154(b) by 339 days.

(21) Appl. No.: 10/698,617

(22) Filed: Oct. 31, 2003

(51) Int. Cl.
*G02B 6/42* (2006.01)

(52) U.S. Cl. .................. 385/88; 385/117; 385/137; 385/147; 385/123

(58) Field of Classification Search ............ 385/88, 385/117, 147, 137
See application file for complete search history.

(56) References Cited

U.S. PATENT DOCUMENTS

| | | | |
|---|---|---|---|
| 4,646,006 A * | 2/1987 | Schweitzer, Jr. ............ 324/127 |
| 4,974,789 A * | 12/1990 | Milburn ..................... 242/159 |
| 5,235,664 A * | 8/1993 | Okada et al. ............... 385/134 |
| 5,253,412 A * | 10/1993 | Fukuoka et al. ........... 29/566.3 |
| 5,469,611 A * | 11/1995 | Sasaki et al. .............. 29/426.2 |
| 5,524,167 A * | 6/1996 | Ewert et al. ................ 385/137 |
| 6,337,943 B1 * | 1/2002 | Dumitriu ..................... 385/137 |
| 6,628,879 B2 * | 9/2003 | Robinson et al. ........... 385/134 |
| 6,695,191 B1 * | 2/2004 | Tabeling ....................... 225/95 |
| 2002/0145731 A1 * | 10/2002 | Kritler et al. ............... 356/73.1 |
| 2003/0065323 A1 * | 4/2003 | Hess et al. .................... 606/49 |
| 2003/0182881 A1 * | 10/2003 | Denier et al. .............. 52/220.7 |
| 2003/0223712 A1 * | 12/2003 | Chapman et al. ............ 385/96 |
| 2005/0169594 A1 * | 8/2005 | Song ........................... 385/134 |

* cited by examiner

*Primary Examiner*—Frank G. Font
*Assistant Examiner*—James P. Hughes
(74) *Attorney, Agent, or Firm*—Blakely Sokoloff Taylor & Zafman LLP

(57) ABSTRACT

A method and apparatus for a universal single handed light cable receptive port is disclosed. In one embodiment, a jaw assembly is coupled to a base. A latch is coupled to a base to hold the jaw assembly open and to define an aperture. When a cable is inserted into an aperture the latch is released and the jaw assembly is closed to secure the cable. In another embodiment, a release mechanism is coupled to a jaw assembly to open the jaw assembly to release the cable and engage the latch. In a further embodiment, an actuator is coupled to the base, the actuator is to receive cable and release the latch when depressed by the cable.

19 Claims, 4 Drawing Sheets

UNIVERSAL INTERFACE FOR SINGLE-HANDED INSERTION OF CABLES

FIELD OF THE INVENTION

The present invention pertains to the field of endoscopic camera systems. More particularly, the present invention relates to a method and apparatus for a universal interface allowing single-handed insertion of light cables.

BACKGROUND

Endoscopy is a medical field in which internal features of a body are viewed without the use of traditional, fully-invasive techniques. In medicine, endoscopy is now widely used to perform minimally invasive surgical procedures, such as arthroscopy and laparoscopy. A basic endoscopy tool is the endoscopic camera system, which includes a scope that is inserted into the body of a patient and a camera coupled to the scope. Images acquired by the camera are typically displayed on a conventional video monitor.

The camera requires light when endoscopic procedures are performed. The light is typically is supplied through a fiber-optic light cable which is connected with a light source unit. The light cable may need to be inserted or changed during surgery for various reasons. To provide light to the light cable, one end of the cable is plugged into the light source unit by an operating room (OR) staff member. When inserting a light cable into a light source unit, the staff member's hands that touch the light source will no longer be sterile. It is therefore desirable to reduce the amount of contact necessary by a person with a light source to insert a light cable. Specifically, one handed operation is desirable.

Further, light cables made by different manufactures tend to come in a wide variety of diameters and sizes. An OR may require a light source unit to be compatible with different sized cables. It is therefore desirable to have a light source unit that can accept a wide variety of sizes of light cables.

A previous implementation of a universal light source unit interface for accepting light cables included a jaw assembly and a handle. The jaw assembly was opened using the handle. When an OR staff member wanted to insert a light cable into a light source unit, the staff member rotated the handle to open the assembly. The light cable was then inserted into the aperture created by the opened jaw assembly. This implementation allow for universal acceptance of light cables, however it required two-handed operation to insert and remove the light cables.

Another prior implementation allows for single-handed insertion of light cables into a light source unit. This implementation included one or more ports mounted on a turret that can accept a light cable. Each of the ports had a specific diameter, and each of the ports was designed to accept a specific size light cable. An OR staff member had to first index the turret to the appropriate port then manually insert a light cable. This implementation allowed for single-handed insertion, however it required the staff member to touch the light source for port selection, thereby breaking the sterile field, and the implementation also limits the sizes of light cables that can be used. Further, if there are several ports on the face of a light source unit, an OR staff member may not be able to quickly locate the appropriate port.

SUMMARY OF THE INVENTION

The present invention includes an apparatus that comprises a jaw assembly coupled to a base. A latch is coupled to a base to hold the jaw assembly open and to define an aperture. When a cable is inserted into an aperture the latch is released and the jaw assembly is closed to secure the cable.

DETAILED DESCRIPTION

A universal interface for a single-handed insertion of cables is disclosed. The interface allows an operating room (OR) staff member to insert light cables of various sizes into a light source unit using one hand. This interface allows a surgical team to insert a light cable without touching the light source and in turn breaking the sterile field.

Figure 1:
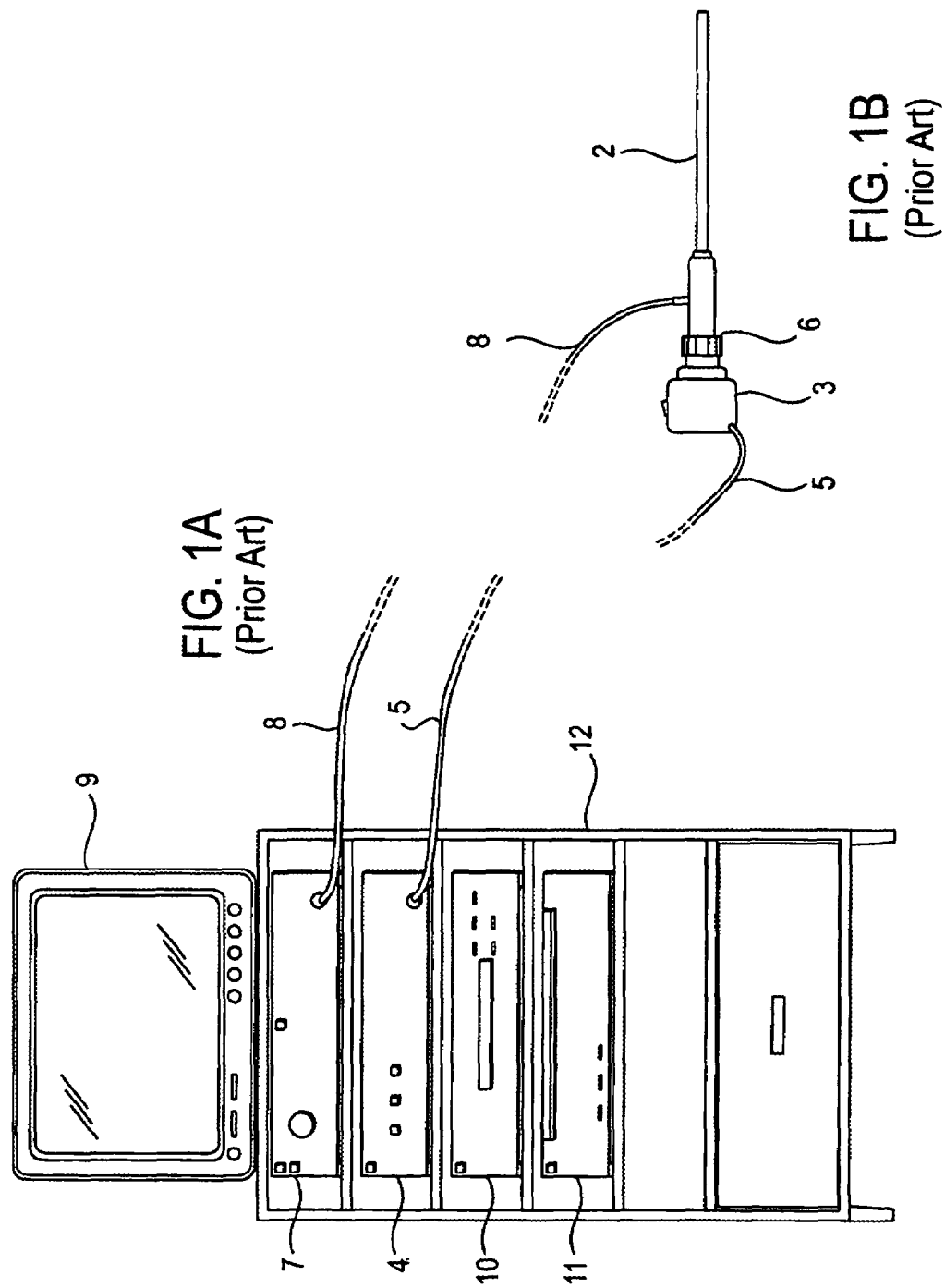
FIGS. 1A and 1B collectively illustrate a typical, conventional endoscopic camera system.

FIGS. 1A and 1B collectively illustrate a typical, conventional endoscopic camera system. FIG. 1A generally illustrates the image generation and display components of the system, while FIG. 1B illustrates the data acquisition components of the system. Referring to FIG. 1B, the data acquisition components include an endoscope (scope) 2, a camera 3, and a coupler 6 connecting the scope 2 to the camera 3. The illustrated scope 2 is a rigid scope of the type commonly used for laparoscopy or artheroscopy. Camera 3 acquires color video image data of internal features of a body through a system of lenses within the scope 2.

Referring to FIG. 1A, in the illustrated embodiment, the image generation and display components of a system include a camera control unit (CCU 4), a light source unit 7, a monitor 9, a digital video recorder (DVR) 10, and a printer 11, which is stored on a mobile cart 12. Light is provided to the scope 2 by the light source unit 7 through appropriate flexible light conduit 8 such as a fiber optic cable. Operation of the camera system may be controlled by CCU 4. The camera 3 is coupled to the CCU 4 by flexible transmission line 5. Transmission line 5 conveys video image data from the camera 3 to the CCU 4 and conveys various control signals bi-directionally between the camera 3 and the CCU 4. Image data received by the CCU 4 from the camera 3 are processed and converted to video images by the CCU 4, which are displayed on monitor 9, recorded by the DVR 10, and/or used to generate static images that can be printed by printer 11.

During a surgical procedure, a light cable 8 may be inserted into the light source unit 7 by an OR staff member. When the staff member touches the light source unit 7, the staff member's hand is no longer sterile, and must be re-sterilized. In order to reduce the amount of sterilization necessary, it is desirable to reduce contact with the light source unit 7, and it is therefore desirable to allow one-handed insertion of the light cable 8.

Figure 2:
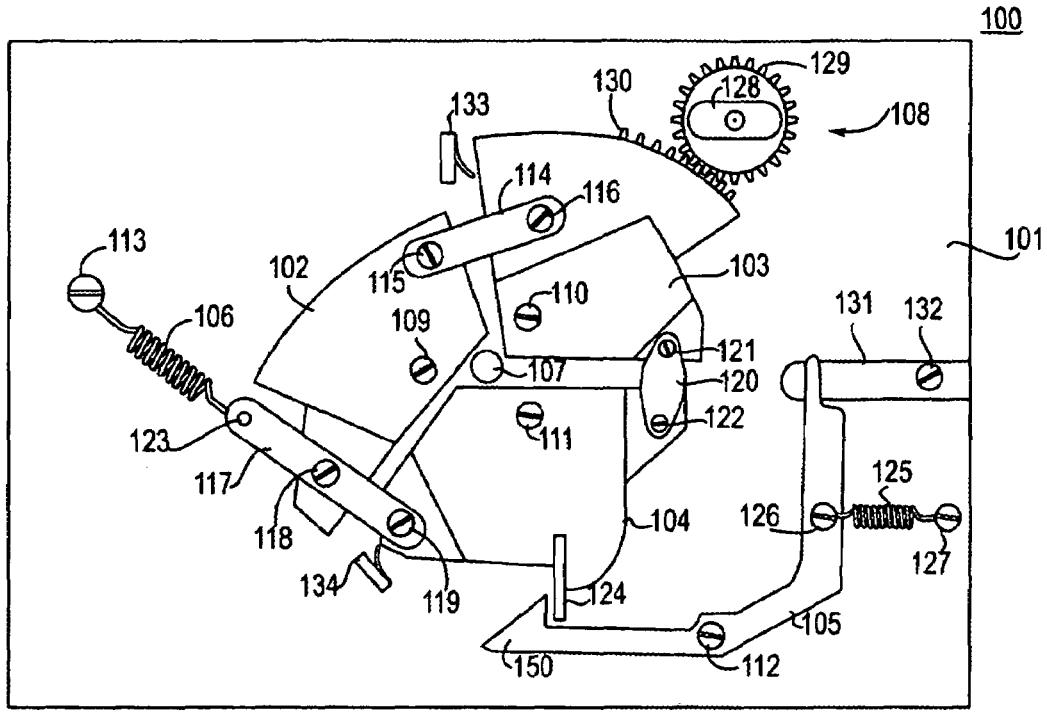
FIG. 2 illustrates the front view of a universal interface for single-handed insertion of cables, according to one embodiment of the invention.

FIG. 2 illustrates the front view of a universal interface for single-handed insertion of cables, according to one embodiment of the invention. The interface 100 includes a base 101, a jaw assembly comprising jaws 102, 103, and 104, a latch 105, a spring 106, a plunger actuator 107, and a release mechanism 108. The interface 100 may be integrated into a front panel or other convenient location on a light source unit 7 to accept a light cable 8.

The jaws 102, 103, and 104, the latch 105, and the spring 106 are coupled to the base 101 using bolts 109, 110, 111, 112, and 113, respectively. The jaw 102 is coupled to the jaw 103 using an arm 114. The arm 114 is connected to the jaws 102 and 103 using screws 115 and 116, respectively. Likewise, the jaw 102 is coupled to the jaw 104 using arm 117. The arm 117 is coupled to the jaws 102 and 104 using screws 118 and 119, respectively. The jaws 103 and 104 are coupled together using an arm 120, which is coupled to the jaws 103 and 104 using screws 121 and 122, respectively. The spring 106 is attached to the jaw assembly using the arm 117. An eye 123 in one end of the arm 117 couples the spring 106 between the arm 117 and the bolt 113. The jaw 104 may also include an insert 124.

The latch 105 is coupled to the base 101 through the bolt 112. The latch 105 is also coupled to a spring 125 through a screw 126. The spring 125 is coupled to the base 101 using screw 127. The release mechanism 108 includes a shaft 128 and a pinion 129. The pinion 129 engages with a gear portion 130 of the jaw 103. The base 101 includes a slot 131 which is open to the backside of the base 101. A shaft 132 protrudes through the slot 131.

The jaws 102, 103, and 104 pivot about the bolts 109, 110, and 111, thereby allowing a user to rotate the jaws opened using the release mechanism 108. When the release mechanism 108 is rotated using the shaft 128, the pinion 129 engages the gear portion 130, rotating the jaw 103 about the bolt 110. The arm 114 then moves laterally, causing the jaw 102 to rotate about the bolt 109. Similarly, the jaw 104 is rotated about the bolt 111. The jaws 102, 103, and 104 generally have two positions, an opened position and a closed position. The opened position defines an aperture to accept a light cable 8. As shown in FIG. 2, the jaws 102, 103, and 104 are in the opened position. That is, the jaws 102, 103, and 104 are ready to accept a light cable 8. When a light cable 8 is inserted, the jaws 102, 103, and 104 will close, thereby securing the light cable 8.

The spring 106 is connected at one end to the base 101 and at the other end to the arm 117. The spring provides a spring force upon the jaws 102, 103, and 104, and tends to make the jaws 102, 103, and 104 rotate closed. The latch 105 pivots about the bolt 112. The latch 105 engages the jaws 102, 103, and 104 to hold them open. A barb end 150 of the latch 105 holds the liner 124, and therefore the jaws 102, 103, and 104 in the opened position. In one embodiment, the liner 124 comprises a material such as polytetrafluoroethylene (PTFE), and may be inserted into the jaw 104 in order to reduce wear upon the jaw 104 and the latch 105. Since the barb end 150 holds the jaw 104 in place, the other jaws 102 and 103 are also held in place, since the jaws 102, 103, and 104 are interconnected using the arms 114, 117, and 120. The spring 125 holds the latch 105 closed.

Electrical switches 133 and 134 can detect when the jaws 102, 103, and 104 are opened or closed. In one embodiment, electrical switches 133 and 134 are wired together in series and mounted to the base 101. When the jaws 102, 103, and 104 are opened, the light source does not need to be on, since there is no light cable 8 inserted. However, when the jaws 102, 103, and 104 are closed, it is assumed that a light cable 8 is inserted and that the light source should be on. The switches 133 and 134 can thereby cause the light source to turn on. In another embodiment, only one of switches 133 or 134 is necessary. A second switch 133 or 134 can be used to detect whether the jaws 102, 103, and 104 are fully closed. This may be necessary if a user removes the light cable 8 without rotating the release mechanism 108. If this happens, the plunger actuator 107 may not return to the ready position and the jaws 102, 103, and 104 may completely close. Although this is not the intended operation, a second switch 133 or 134 can cause the light to be extinguished.

The plunger actuator 107 receives a cable 8 when it is inserted. The plunger actuator 107 is coupled to the backside of the base 101. The plunger actuator 107 has a ready position and a depressed position. When the jaws 102, 103, and 104 are opened, the plunger actuator 107 has a plunger portion extending through the opened jaws 102, 103, and 104, and is in the ready position. When a light cable 8 is inserted from above the plunger actuator 107, the plunger actuator 107 is depressed, and held in the depressed position. The plunger actuator 107 is shown in the ready position in FIG. 3. In one embodiment, the plunger actuator 107 also has a channel running through it to allow light to pass from the light source through the plunger actuator 107 and into an inserted light cable 8.

When a light cable 8 is inserted between the jaws 102, 103, and 104, the light cable 8 will depress the plunger actuator 107. When the plunger actuator 107 is depressed, the plunger actuator 107 will cause the shaft 132 to move laterally through the slot 131 toward the latch 105. The plunger actuator 107 causes a slide actuator, to which the shaft 132 is mounted on the backside of the base 101, to move inward when the plunger actuator 107 is depressed. The spring 125 biases the latch 105 into an engaged position to hold the jaws 102, 103, and 104 open. However, when a light cable 8 is inserted between the jaws 102, 103, and 104, and the plunger actuator 107 is depressed, the shaft 132 is moved, and pressed against the latch 105. When the shaft 132 contacts the latch 105, the latch 105 disengages the insert 124, the latch 105 is released, and the spring 106 biases the jaws 102, 103, and 104 closed. When the jaws 102, 103, and 104 close, the light cable 8 is still inserted between them, and the light cable 8 is secured. The inner edges of jaws 102, 104, and 106 may be serrated in order to increase the holding a force of the jaws 102, 104, and 106.

Since the latch 105 holds the jaws 102, 103, and 104 open when no cable is inserted, an OR staff member needs only one hand to insert the light cable 8 and to secure it. Further, since the jaws 102, 103, and 104 are continuously adjustable with respect to each other within a certain range, the jaws 102, 103, and 104 can accept a light cable 8 of any size within a certain range.

When an OR staff member wants to release an inserted light cable 8, the staff member can rotate the release mechanism 108 counterclockwise. The release mechanism 108 will then rotate the jaws 102, 103, and 104 open, causing the light cable 8 to be released. Further, the latch 105 will slide along the insert 124 until the latch 105 is reengaged. Therefore, when the staff member rotates the release mechanism 108, the light cable 8 will be released, the jaws 102, 103, and 104 will be opened and the latch 105 will reengage, thereby holding the jaws 102, 103, and 104 open. In this way the interface 100 is reset, and another light cable 8 can then be inserted. The release mechanism 108 also requires only one-handed operation in order to open the jaws and release the light cable 8.

Figure 3:
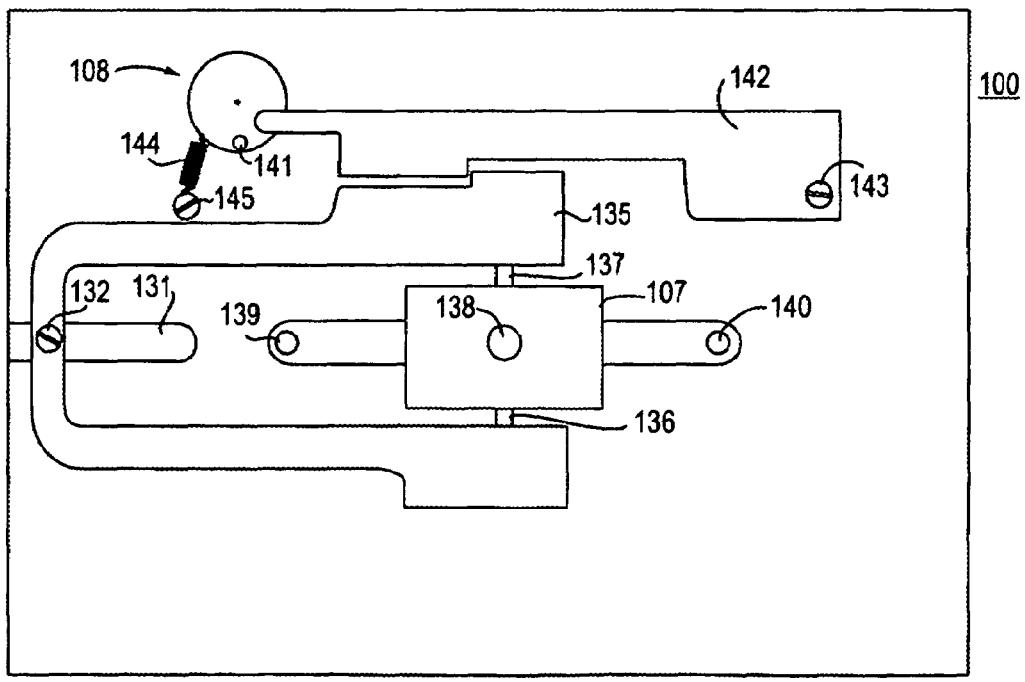
FIG. 3 illustrates the back side of the interface (i.e., the view of the opposite side of the view shown in FIG. 2).

FIG. 3 illustrates the back side of the interface 100 (i.e., the view of the opposite side of the view shown in FIG. 2). When a light cable 8 is inserted, the plunger actuator 107 moves back into the light source unit 7. A slide actuator 135 is coupled to the plunger actuator 107. Two pins 136 and 137 extend out of the slide actuator 135 and into the plunger actuator 107. When the plunger actuator 107 is depressed by the insertion of the light cable 8, the slide actuator 135 moves inward, toward the center of the interface 100. The shaft 132 is attached to one end of the slide actuator 135 and extends through the slot 131 to the front side of the interface 100. When the plunger actuator 107 is depressed, the pins 136 and 137 move through diagonal grooves in the plunger actuator 107, causing the slide actuator 135 and the shaft 132 to move inward and release the latch 105. As a result, when a cable 8 is inserted and depresses the plunger actuator 107, the slide actuator 135 is moved inward and the latch 105 is released when the shaft 132 contacts the latch 105. When the latch 105 is released, the jaws 102, 103, and 104 close, thereby securing the cable 8.

The plunger actuator 107 further includes a channel 138 to direct light from the light source unit 7 into the light cable 8. The plunger actuator 107 slides back and forth along two shafts 139 and 140. When the light cable 8 is inserted, the plunger actuator 107 moves into and is held in the depressed position. Two springs, mounted along the shafts 139 and 140 beneath the plunger actuator 107, bias the plunger actuator into the ready position.

The backside of the release mechanism 108 has a pin 141 in it. When the release mechanism 108 is rotated to release the light cable 8 the pin 141 contacts and releases a slide retainer 142. The slide retainer 142 is coupled to the base 101 using a screw 143. The slide retainer 142 also pivots about the screw 143. The slide retainer 142 normally holds the slide actuator 135 in position when the cable 8 is inserted. The slide retainer 142 also causes the plunger actuator 107 to remain in the depressed position, because it holds the slide actuator 135 in position. When the release mechanism 108 is rotated, the pin 141 contacts the slide retainer 142 and releases the slide retainer 142, thereby releasing the slide actuator 135 and causing the plunger actuator 107 to return to the ready position. Since the plunger actuator 107 slides back and forth along two shafts 139 and 140 having springs upon them, the springs extend returning the plunger actuator 107 to the ready position. In one embodiment, the slide retainer 142 keeps the plunger actuator 107 in a depressed position after the cable has been released until the jaws 102, 103, and 104 are fully opened. The spring 144 is mounted to the base 101 using a screw 145. The spring 144 returns the release mechanism 108 to a ready position after the user releases the turret 128.

Figure 4:
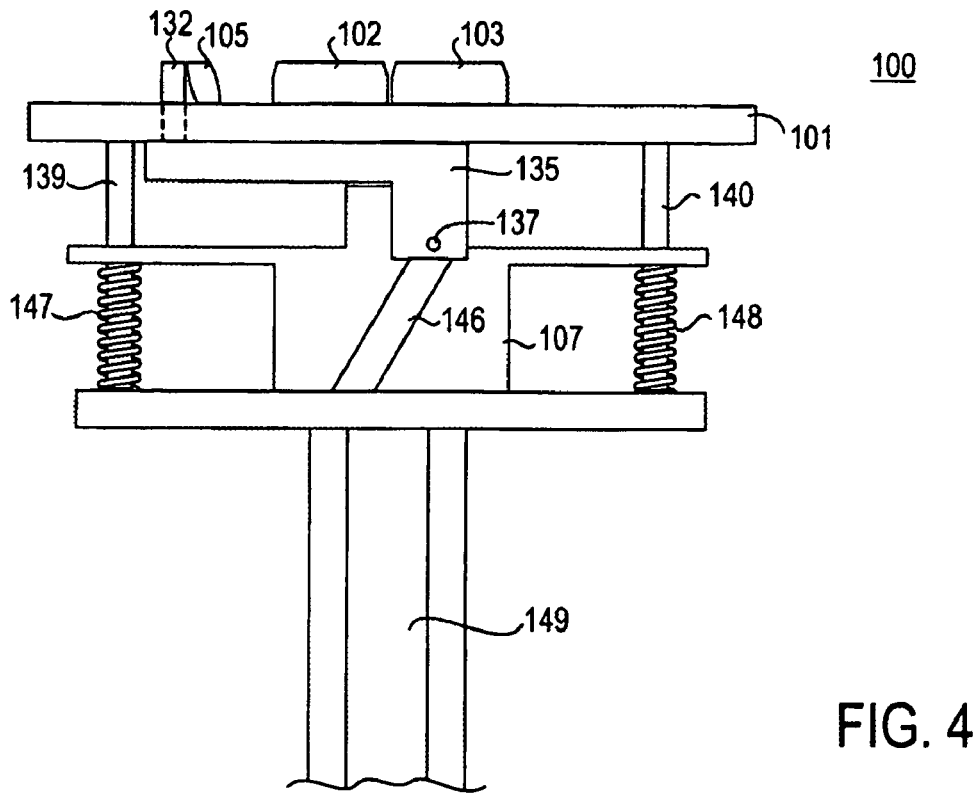
FIG. 4 illustrates an overhead view of the jaw assembly, with the plunger actuator in the depressed position.

FIG. 4 illustrates an overhead view of the jaw assembly, with the plunger actuator 107 in the depressed position. When the plunger actuator 107 moves into the depressed position and the jaws 102, 103, and 104 are closed to secure the light cable 8, the slide actuator 135 is pulled inward so that the shaft 132 is holding the latch 105 open. The pin 137 slides in a slot 146 in the top of the plunger actuator 107. Likewise, the pin 136 slides in a slot in the bottom of the plunger actuator 107. When the plunger actuator 107 is depressed, the pin 137 is moved through the slot 146, causing the slide actuator 135 to move the shaft 132 toward the latch 105, thereby releasing the latch 105 and holding it in place, causing the jaws 102, 103, and 104 to close. The plunger actuator 107 slides along the two shafts 139 and 140. Two springs 147 and 148, along the shafts 139 and 140, bias the slide actuator 107 into the ready position. When the light cable 8 is inserted and the plunger actuator 107 is depressed, the plunger actuator 107 is held in the depressed position by the force of the light cable 8 which is being held by the jaws 102, 103, and 104.

A channel 149 directs light from a light source through the channel 138 in the plunger actuator 107. This light is then directed into the light cable 8. The light source is activated when the switches 133 and 134 indicate that the jaws 102, 103, and 104 are closed, thereby indicating that a light cable 8 has been inserted.

Figure 5:
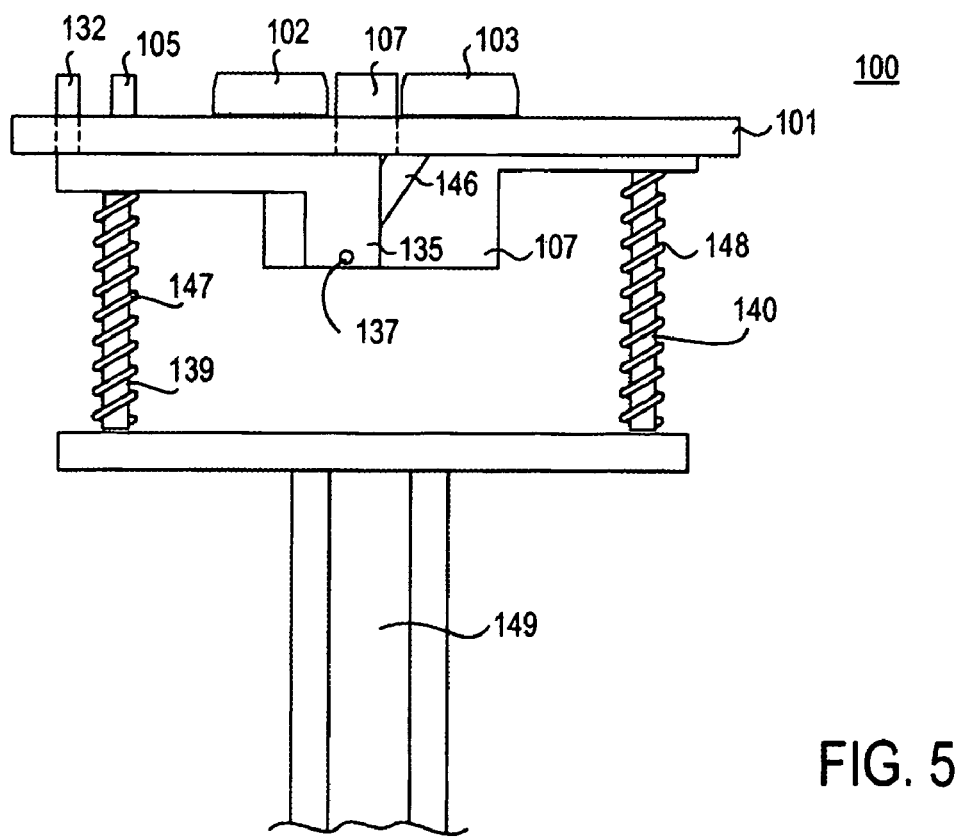
FIG. 5 illustrates an overhead view of a jaw assembly in an open position.

FIG. 5 illustrates an overhead view of a jaw assembly in an open position. When the jaws 102, 103, and 104 are open and ready to receive a light cable 8, the plunger actuator 107 is in the ready (not depressed) position and is extended through the aperture defined by the jaws 102, 103, and 104. When the plunger actuator 107 is in the ready position, the pin 137 slides to the far end of the slot 146, thereby moving the slide actuator 135 toward the outside edge of the base 101. The shaft 132 is not engaging the latch 105 and the latch 105 remains engaged to the jaws 101, 102, and 103, thereby holding them open.

Figure 6:
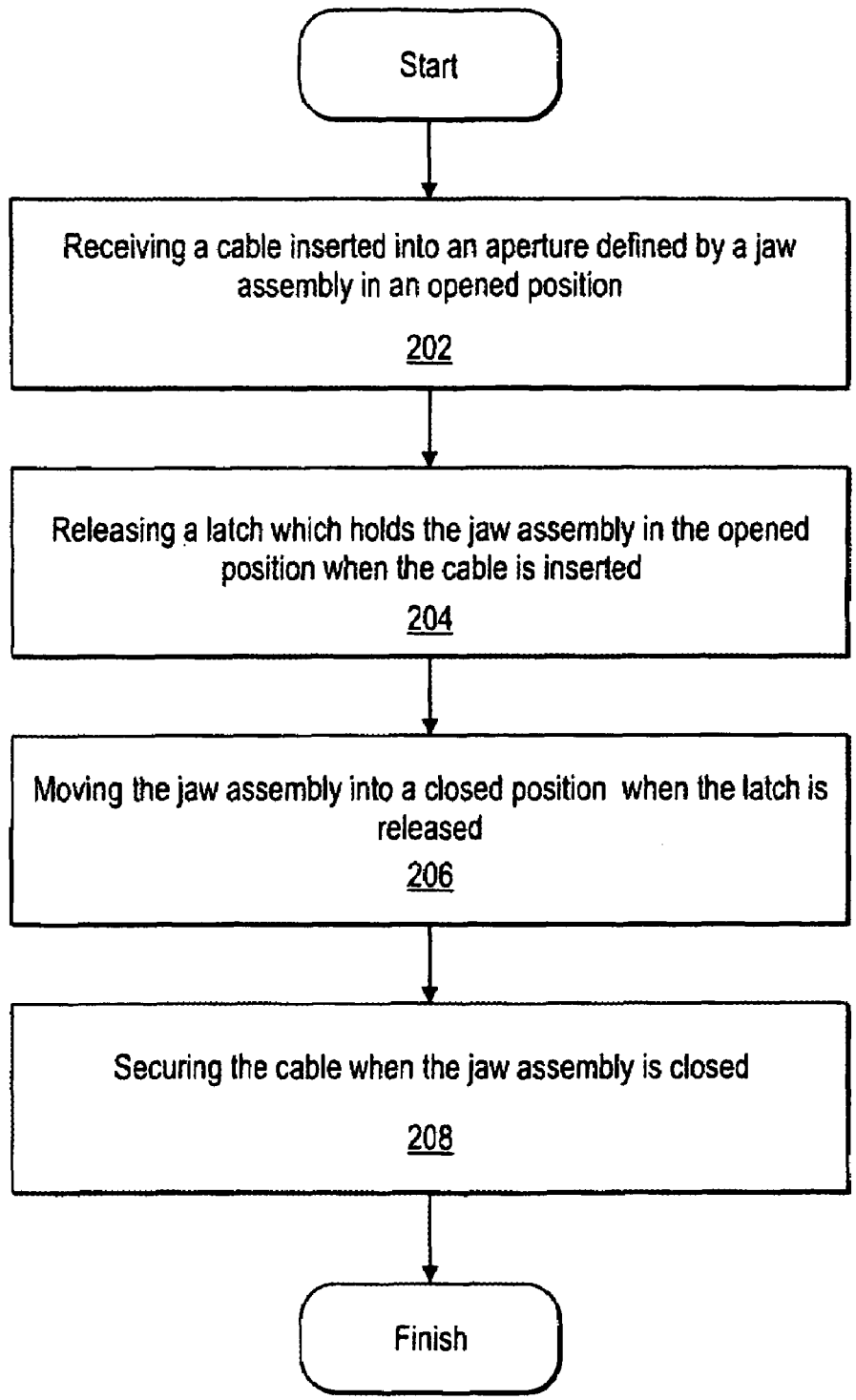
FIG. 6 is a flow chart illustrating a sequence of events performed by the jaw assembly during the insertion of a cable into a jaw assembly.

FIG. 6 is a flow chart illustrating a sequence of events performed by the jaw assembly during the insertion of a cable into a jaw assembly. In block 202, a light cable is received after it is inserted into an aperture defined by a jaw assembly in an open position. A light cable 8 is received by a plunger actuator 107 inserted through the set of jaws 102, 103, and 104 in an opened position. In block 204, the latch 105, which is holding the jaw assembly in the open position, is released when the cable is inserted. The latch 105 is released after the plunger actuator 107 is depressed, thereby laterally moving the slide actuator 135, causing the shaft 132 to engage the latch 105, releasing the latch 105. In block 206, the jaw assembly is moved into the closed position when the latch is released. Once the latch is released, the spring 106 will pull the jaws 102, 103, and 104 together so as to close them upon a light cable 8. In block 208, the light cable 8 is secured when the jaw assembly is closed. The jaws 102, 103, and 104 close upon a light cable 8 holding it in place.

A light source unit interface which allows one-handed insertion of a variety of sizes of light cables has been disclosed. The light source unit interface includes a rotatable jaw assembly having an opened and a closed position. In the opened position, the jaw assembly is ready to accept a light cable. A latch holds the jaw assembly in the opened position. A light cable can then be inserted between the jaws. A plunger actuator is depressed by the cable, and the plunger actuator causes a slide actuator to release the latch, thereby closing the jaws and securing the cable. A release mechanism can be manipulated to release the cable and move the jaw assembly to the open position, thereby reengaging the latch.

Other embodiments of the disclosed invention may also be practiced. For example, the switches 133 and 134 or the insert 124 may be omitted. In other embodiments, alternate structures for releasing the latch 105 may be used. One skilled in the art would understand that various alternative structures may be used to the same effect.

This invention has been described with reference to specific exemplary embodiments thereof. However, various modifications and changes may be made to these embodiments without departing from the broader spirit and scope of the invention. The specification and drawings are accordingly, to be regarded in an illustrative rather than a restrictive sense.

What is claimed is:

1. An apparatus, comprising:
    a base;
    a jaw assembly coupled to the base;
    a latch coupled to the base to hold the jaw assembly open, the jaw assembly defining an aperture when open, the latch to allow the jaw assembly to close around a cable automatically to secure the cable in response to insertion of the cable into the aperture, wherein the cable is a light cable for transmitting light;
    an actuator coupled to the base to release the latch when the actuator is depressed by the cable, wherein the actuator includes a first channel to allow light to pass through the actuator; and
    a second channel coupled to the base and to a light source to supply light to the first channel and to the light cable.

2. The apparatus of claim 1, further comprising a release mechanism coupled to the base and to the jaw assembly to open the jaw assembly, so as to release the cable and engage the latch.

3. The apparatus of claim 1, further comprising a liner coupled to the jaw assembly to engage the latch.

4. The apparatus of claim 1, wherein the jaw assembly further comprises a serrated inner edge to engage the cable.

5. The apparatus of claim 1, further comprising a switch coupled to the base to detect when the jaw assembly is open and to turn off the light source in response to the jaw assembly being open.

6. The apparatus of claim 1, further comprising a spring coupled to the base and the jaw assembly to hold the jaw assembly open.

7. The apparatus of claim 1, further comprising a retainer to retain the actuator when the cable is released is used until the jaw assembly is fully opened.

8. A method comprising:
    receiving a light transmission cable inserted into an aperture defined by a jaw assembly in an opened position;
    releasing a latch which holds the jaw assembly in the opened position automatically in response to the light transmission cable being inserted into the aperture;
    moving the jaw assembly into a closed position around the light transmission cable in response to the latch being released, so as to secure the light transmission cable in the jaw assembly;
    activating a switch after the light transmission cabled is secured in the jaw assembly;
    activating a light source coupled with the actuator in response to activating the switch; and
    directing light from the light source through the actuator and into the light transmission cable.

9. The method of claim 8, wherein releasing the latch comprises depressing an actuator in the aperture when the light transmission cable is inserted and releasing the latch with the actuator.

10. The method of claim 9, further comprising:
    releasing the light transmission cable by opening the jaw assembly using a release mechanism;
    engaging the latch and holding the jaw assembly in the opened position; and
    returning the actuator to the aperture.

11. An apparatus comprising:
    means for receiving a cable inserted into an aperture defined by a jaw assembly in an opened position;
    means for releasing a latch which holds the jaw assembly in the opened position automatically when the cable is inserted;
    means for moving the jaw assembly into a closed position in response to the latch being released;
    means for securing the cable when the jaw assembly is closed;
    means for activating a switch;
    means for activating a light source coupled with the actuator in response to activation of the switch; and
    means for directing light from the light source through the actuator and into the cable.

12. The apparatus of claim 11, wherein the means for releasing the latch comprises means for depressing an actuator in the aperture when the cable is inserted and means for releasing the latch with the actuator.

13. The apparatus of claim 12, further comprising:
    means for releasing the cable by opening the jaw assembly;
    means for engaging the latch and holding the jaw assembly in the opened position; and
    means for returning the actuator to the aperture.

14. An apparatus comprising:
    a base;
    a jaw assembly coupled to the base, the jaw assembly to define an aperture when opened;
    a spring coupled to the jaw assembly and the base, the spring to hold the jaw assembly open;
    a plunger actuator having a plunger portion to extend through the aperture, the plunger actuator to receive a cable;
    a slide actuator coupled to the plunger actuator and the base, wherein the slide actuator is actuated by the plunger actuator when a cable is inserted into the aperture;
    a latch coupled to the base to hold the jaw assembly open, wherein the latch is released by the slide actuator when the cable is inserted in the aperture, and wherein the jaw assembly is closed and the cable is secured when the latch is released;
    a release mechanism coupled to the base and to the jaw assembly, the release mechanism to open the jaw assembly, release the cable, and move the plunger portion of the plunger actuator into the aperture.

15. The apparatus of claim 14, wherein the jaw assembly further comprises an insert to engage the latch.

16. The apparatus of claim 14, wherein the cable is a light cable for transmitting light.

17. The apparatus of claim 16, wherein the plunger actuator includes a channel to allow the transmission of light.

18. The apparatus of claim 17, further comprising a second channel coupled to the base and to a light source to supply light to the channel and the light cable.

19. The apparatus of claim 18, further comprising a switch coupled to the base to detect when the jaw assembly is open and to turn off the light source in response to the jaw assembly being open.

* * * * *